United States Patent [19]

Ekins et al.

[11] Patent Number: 4,745,072
[45] Date of Patent: May 17, 1988

[54] IMMUNOASSAY AND IMMUNOMETRIC ASSAY OF FREE LIGAND CONCENTRATIONS IN BIOLOGICAL FLUIDS

[76] Inventors: Roger P. Ekins; Thomas M. Jackson, both of Department of Molecular Endocrinology, The Middlesex Hospital School of Medicine, Mortimer Street, London, England, W1N 8AA

[21] Appl. No.: 705,421
[22] PCT Filed: Jun. 22, 1984
[86] PCT No.: PCT/GB84/00220
§ 371 Date: Feb. 20, 1985
§ 102(e) Date: Feb. 20, 1985
[87] PCT Pub. No.: WO85/00226
PCT Pub. Date: Jan. 17, 1985

[30] Foreign Application Priority Data

Jun. 23, 1983 [GB] United Kingdom ............... 8317124

[51] Int. Cl.⁴ .................. G01N 33/53; G01N 33/534; G01N 33/546; G01N 33/78
[52] U.S. Cl. ............................ 436/500; 436/501; 436/534; 436/545; 436/804; 436/817
[58] Field of Search ............... 436/500, 501, 504, 505, 436/517, 518, 536, 540, 815, 817, 819, 825, 534, 545, 804; 424/1.1

[56] References Cited

U.S. PATENT DOCUMENTS

| | | | |
|---|---|---|---|
| 4,366,143 | 12/1982 | Midgley et al. | 436/501 |
| 4,376,110 | 3/1983 | David et al. | 436/513 |
| 4,381,291 | 4/1983 | Ekins | 424/1 |
| 4,522,922 | 6/1985 | Carro | 436/500 |
| 4,536,479 | 8/1985 | Vander-Mallie | 436/527 |

FOREIGN PATENT DOCUMENTS

| | | |
|---|---|---|
| 026103 | 4/1981 | European Pat. Off. |
| 073865 | 3/1983 | European Pat. Off. |
| 8303306 | 9/1983 | PCT Int'l Appl. |
| 8401031 | 3/1984 | PCT Int'l Appl. |
| 2085160 | 4/1982 | United Kingdom |

OTHER PUBLICATIONS

Free Hormones in Blood: The Concept and the Measurement, Roger P. Ekins, Journal of Clinical Immonoassay, Summer 1984, pp. 163–180.

*Primary Examiner*—Sidney Marantz
*Attorney, Agent, or Firm*—Steele, Gould & Fried

[57] ABSTRACT

A method of measuring the concentration of a free ligand in a biological fluid containing the free ligand and ligand bound to endogenous binding agent, by the steps of (a) mixing a sample of the fluid with an analogue of the ligand, a specific binder with which the free ligand and the ligand analogue bind, and an exogenous binding agent which binds the ligand analogue but not the ligand, either the ligand analogue or the specific binder being labelled,
(b) incubating the resulting mixture,
(c) determining either the amount of the labelled analogue bound or the amount of labelled specific binder bound, or not bound, to the ligand analogue, and
(d) correlating the determined amount to the amount of free ligand present in the sample.

The method is useful to measure concentration of free thyroid hormones and other hormones in body fluids, employing antibodies specific to the ligand analogue as the exogenous binding agents.

13 Claims, 2 Drawing Sheets

IMMUNOASSAY AND IMMUNOMETRIC ASSAY OF FREE LIGAND CONCENTRATIONS IN BIOLOGICAL FLUIDS

TECHNICAL FIELD

The present invention relates to a method for measuring the concentration of free ligand in a biological fluid containing free ligand and ligand bound to endogenous binding agent.

BACKGROUND ART

Immunoassay techniques have been developed in recent years to measure concentrations of free hormones and other ligands in sera and other biological fluids which contain free ligand in equilibrium with ligand bound to endogenous binding agents such as binding proteins. They are based on the principle that if a specific binder for the ligand, usually an antibody, is brought into contact with the sample to be tested the extent of occupancy of the binding sites on the specific binder by the ligand is a measure of the concentration of free ligand, provided that the amount of specific binder is sufficiently low that the equilibrium between free and endogenously bound ligand is not significantly affected. By measuring the extent of occupancy for the unknown sample and calibrating such a measurement using standard samples containing known free ligand concentrations it is possible to determine the free ligand concentration in the unknown sample.

Initially, the extent of occupancy of binding sites was measured by removing the specific binder containing bound ligand from the sample and determing the proportion of unoccupied sites by back-titration using an appropriately labelled material (e.g. radioactively labelled material) which binds at the unoccupied sites. The process was thus effectively a two-step process.

Subsequently it has been proposed to carry out the 'back-titration' without removing the specific binder from the sample, thus converting the two-step process into a one-step process. This can be done either by using as the labelled material a labelled analogue of the ligand or by using as the labelled material a specific binding agent.

Thus, it has been proposed in published European Patent Application No. 0,026,103 which is equivalent to U.S. Pat. No. 4,366,143 of Midgley et al to measure the concentration of free ligand in such a biological fluid by a radioimmunoassay technique comprising (a) admixing a sample of the fluid with a labelled derivative of the ligand and with a specific binder for the ligand, (b) effecting reaction between the free ligand, the labelled derivative and the specific binder, (c) if necessary, separating that portion of the ligand and labelled derivative that has become bound to the specific binder from that portion not so bound, (d) measuring the amount of the labelled derivative that is, or is not, bound to the specific binder, and (e) using that measurement to determine the concentration of free ligand in the biological fluid. According to the process disclosed there, the labelled derivative of the ligand is chosen to bind strongly to the added specific binder but to bind not at all, or much more weakly than does the ligand, to the endogenous binding agent.

In an alternative procedure a method of determining the free ligand concentration involves an immunoradiometric assay comprising admixing a sample of the fluid with a labelled specific binder and an unlabelled analogue of the ligand, incubating the resulting mixture to permit the free ligand and the unlabelled analogue to compete for the labelled specific binder, determining the amount of labelled specific binder bound either to the ligand or to the unlabelled ligand analogue, and correlating the amount of bound labelled specific binder to the amount of free ligand present in the sample.

However when practical assay kits embodying the principles of EPA No. 0,026,103 have been employed to assay free thyroid hormone in samples taken from patients suffering, for example, from certain non-thyroidal illnesses or having serum protein abnormalities unrelated to free thyroid hormone concentration, the assay results appear to show an anomalous free thyroid hormone concentration, contrary to the correct position. It has also been found that the concentration of antibody (acting as specific binder) in those kits can be up to 100 times greater than would have been expected on the simplified theoretical explanation of this technique hitherto proposed.

Further investigation into the operation of those kits has revealed that, far from the ligand analogue being totally unbound to endogenous binding agents or being bound to only a small extent, it is bound to a very substantial extent, at least 90% and probably as much as 99%, not only to the albumin present in the sample but also to the other binding proteins TBG and TBPA.

It is therefore an object of the present invention to devise an alternative and improved technique for assaying free ligand concentrations which is not subject to the disadvantages inherent in the previous technique.

DISCLOSURE OF INVENTION

Figure 1:
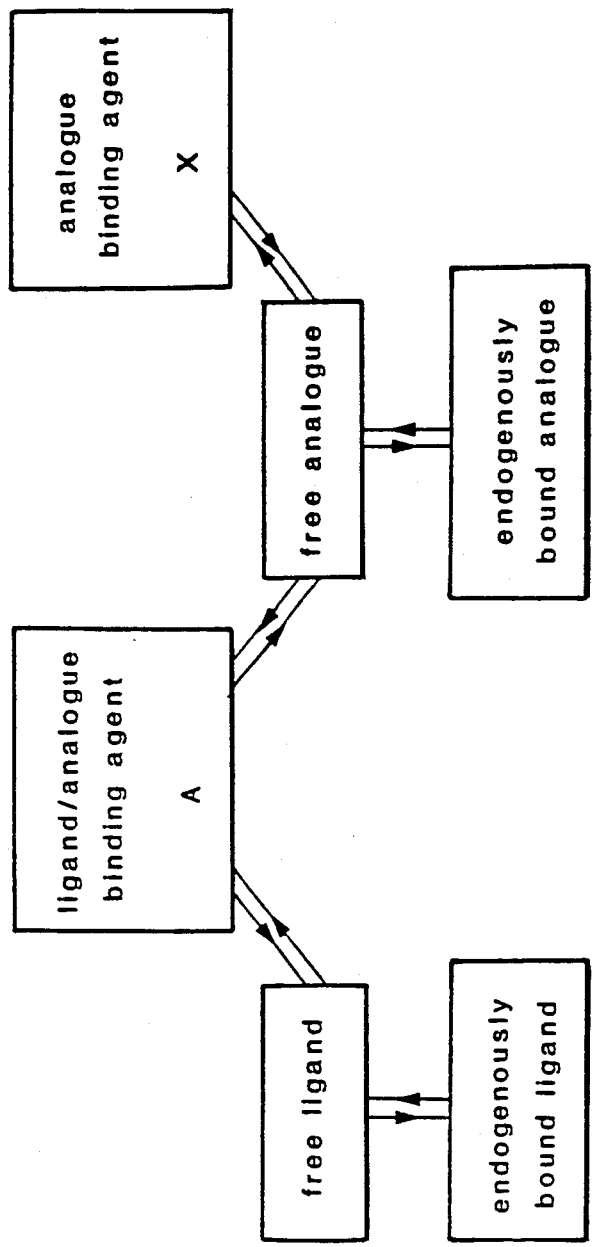
FIG. 1 is a flow diagram illustrating the present invention in terms of competing equilibrium reactions.

It has now been found that, for the immunoassay technique using labelled ligand analogue, when any fraction of the ligand analogue becomes bound to other binding agents in the sample as well as to the specific binder the fraction, b, of the ligand analogue bound to the specific binder is represented by the following equation (provided that the concentration of specific binder is sufficiently low that the equilibrium between free and bound ligand in the sample is not significantly disturbed):

$$b^2 - b\left(\frac{K_H[fH](1 + \Sigma K_p[P])}{K_{An}[An]} + \frac{1 + \Sigma K_p[P]}{K_{An}[An]} + \frac{[Ab]}{[An]} + 1\right) + \frac{[Ab]}{[An]} = 0$$

where, $K_H$ is the equilibrium constant for the ligand/specific binder reaction, $K_{An}$ is the equilibrium constant for the analogue/specific binder reaction,

[fH] is the free ligand concentration,

[An] is the analogue concentration,

[Ab] is the specific binder concentration, $\Sigma K_p[p]$ is $K_{p1}[P_1] + K_{p2}[P_2] \ldots + K_{pn}[P_n]$, $[P_1], [P_2] \ldots [P_n]$ are the concentrations of the various (endogenous or added) binding agents other than Ab in the sample, and $K_{p1}, K_{p2} \ldots K_{pn}$ are the corresponding equilibrium constants for the reactions between the ligand analogue and the various (endogenous or added) binding agents.

A similar equation, in which the term $1 + \Sigma K_p[P]$—hereafter referred to as S—also appears, can be formulated for the immunometric assay technique in which labelled binding agent is used.

On the basis of this theoretical equation it is possible to design an improved assay technique.

Firstly, in situations where the ligand analogue binds with endogenous binding agent and the extent of binding varies from sample to sample of the biological fluid because of variations in the concentration of endogenous binding agent and/or the equilibrium constant for the analogue/endogenous binding agent reaction, it is possible to reduce the significance of those variations by adding a further binding agent (X) having a concentration $[P_x]$ and an equilibrium constant $K_{px}$ for reaction with the analogue such that $K_{px}[P_x]$ contributes significantly to the term S and the contribution to that term from the products $K_{p1}[p_1] \ldots K_{pn}[p_n]$ for the endogenous binding agent(s) is proportionately reduced.

Secondly, even in situations where the ligand analogue does not bind at all or to any significant extent with endogenous binding agent present in the sample or where the concentrations and equilibrium constants for endogenous binding agent do not vary significantly from sample to sample, the addition of a further binding agent for the ligand analogue enables the term S to be increased. The constraints imposed by the equation then allow [Ab] to be increased without sacrificing the accuracy or responsiveness of the technique, which means that the assay can be completed more quickly or that it is possible to use a specific binder of lower specific activity.

According to the invention therefore there is provided an improved method of measuring the concentration of a free ligand in a biological fluid containing the free ligand and ligand bound to endogenous binding agent, comprising (a) mixing a sample of the fluid with an analogue of the ligand, a specific binder with which the free ligand and the ligand analogue bind, and an exogenous binding agent which binds the ligand analogue but not the ligand, either the ligand analogue or the specific binder being labelled, (b) incubating the resulting mixture so that the ligand and ligand analogue compete for the specific binder, (c) determining either the amount of the labelled analogue bound to the specific binder or the exogenous binding agent or the amount of labelled specific binder bound, or not bound, to the ligand analogue, and (d) correlating the determined amount to the amount of free ligand present in the sample.

The exogenous binding agent functions in the method of the present invention as a buffering system for the ligand analogue, having the effect of reducing or eliminating irrelevant fluctuations in the composition of the fluids being tested. Essentially the ligand analogue is the subject of competition between two binding agents, namely the specific binder—hereafter referred to as A—which is also a binder for the ligand, and the exogenous binding agent—hereinafter referred to as X—which is not a binder for the ligand.

Where the contribution to S from the endogenous binding agents is zero or is substantially constant for all samples the exogenous binding agent X and its concentration are advantageously chosen so that $K_{px}[P_x]$ and S are both at least 10, S preferably being 50–500. When the contribution to S from the endogenous binding agents is liable to vary significantly from sample to sample the exogenous binding agent X and its concentration are advantageously chosen so that $K_{px}[P_x]$ is comparable with or larger than the expected variation in S and preferably constitutes at least half of S, for example two thirds to nine tenths of S.

It will be appreciated however that the ranges of optimum utility for the product $K_{px}[p_x]$ as a fraction of S will vary from case to case depending on the clinical acceptability of inaccuracies in the measurement of free ligand and the extent to which the contribution to S from the endogenous binding agents alone is likely to vary.

A practical upper limit on the amount of exogenous binding agent X may often be imposed by the fact that increases in the amount of the exogenous binding agent X will in general be accompanied by increases in the amount of the specific binder A and that too great an increase in the amount of the specific binder A will lead to a significant disturbance of the equilibrium between free and bound ligand in the biological fluid.

Expressed in terms of competing equilibrium reactions, the method of the present invention can be depicted as shown in FIG. 1 of the accompanying drawings. An equilibrium is set up between free ligand, endogenously bound ligand, ligand bound to specific binder A, free ligand analogue, ligand analogue bound to specific binder, ligand analogue bound to exogenous binding agent X and, in the usual case, endogenously bound ligand analogue. Thus the invention differs from the system described in EPA No. 0,026,103 by the provision of a ligand analogue which can be extensively bound to endogenous binding agents and is buffered by the presence of the additional exogenous binding agent X so that the effects of fluctuations in the equilibrium reactions with endogenous binding agents can be proportionately reduced.

The choice of the exogenous binding agent X is dependent upon the nature of the ligand and the ligand analogue because it is essential that it should bind with the ligand analogue and not with the ligand. It is also an essential requirement for this binding agent, as for the specific binder A, that it must not through its inherent nature or its concentration disturb the equilibrium between the free ligand and the endogenously bound ligand, nor must it in turn be influenced by the endogenous binding agent or by drugs or any other ingredients likely to be present in the fluids being tested. The exogenous binding agent X may for example be a physical encapsulation of the analogue. Preferably, however, it will be a reagent, especially an antibody, which is tailored according to the chemical differentiation between the ligand and analogue so as to bind the latter but not the former. Advantageously, the antibody acting as binding agent X does not have a very high affinity for the analogue (provided that its affinity for the ligand is lower by at least about 2 orders of magnitude). Such antibodies may then be used at fairly high concentrations to provide the required value for the product $K_{px}[p_x]$. Those familiar with immunoassay techniques will be able to design an appropriate exogenous binding agent X without difficulty.

The method of the present invention is applicable not only to immunoassay techniques (eg. radioimmunoassay) in which the ligand analogue is labelled (eg. radioactively) but also to immunometric assay techniques (e.g. immunoradiometric assays) in which the specific binder is labelled (e.g. radioactively).

The method may be used to measure concentrations of free hormones in biological fluids, especially free thyroid hormones $T_3$ and $T_4$ but also other hormones such as cortisol, progesterone, oestradiol and testosterone. The specific binders A used may be those known to be useful for this purpose in previous immunoassay techniques or may be formulated according to known principles. The ligand analogues described in EPA No. 0,026,103 and No. 0,073,865 may be used in the method of the present invention, as may other ligand analogues and it will be appreciated that it is no longer necessary to attempt to design a ligand analogue which will not be bound to endogenous binding agents but merely one which can be bound to a binding agent X which does not bind the ligand itself. The ligand analogues can be labelled in any appropriate manner, for example as described in EPA No. 0,026,103 when immunoassay techniques are to be used. Alternatively, the analogues may be used in an unlabelled state together with a labelled specific binder as described in greater detail in International patent application WO 83/03306. The other operational conditions appropriate for the method of the present invention may be the same as those known or conventional in previous immunoassay techniques.

The invention and the improvement achievable by its use, are illustrated by the following example.

EXAMPLE

An analogue of thyroxine ($T_4$) suitable for the immunoassay of free $T_4$ ($fT_4$) as described in EPA No. 0,026,103 was prepared by chemical modification of the amino acid structure of $T_4$. An antibody (X) against this analogue was produced by well known immunological techniques and shown to have a relative affinity for analogue as compared to its affinity for $T_4$ of $10^3$.

The analogue was radiolabelled with $^{125}I$ by the well known "exchange" method and shown to have much lower affinity constants than $T_4$ for the normal $T_4$ binding proteins thus satisfying the requirements of EPA No. 0,026,103.

A specific antibody against $T_4$ (A), with an equal affinity for the modified $T_4$ analogue was coupled to solid particles.

A mixture was prepared of 0.5 ml of a suspension of the solid-phase antibody reagent (2 nm) and 0.5 ml of the $^{125}I$ $T_4$ analogue (2 nM), both diluted in 4% BSA, PBS pH 7.4 and a 100 ul aliquot of normal human serum containing various concentrations of $fT_4$ (prepared by well known techniques). The extent of binding of the $^{125}I$ analogue to the specific binding reagent was correlated with $fT_4$ concentration as shown in FIG. 2(a).

A similar mixture was prepared containing identical concentrations of specific antibody and analogue but with 100 ul aliquots of samples containing 3 nM oleic acid and varying concentrations of $fT_4$. (Oleic acid is one of a class of compounds known as non-esterified fatty acids which are known to be increased in serum samples following the administration of some drugs and during non-thyroidal illness.)

The extent of binding was found to correlate with $fT_4$ as shown in FIG. 2(b). Thus a sample containing, e.g. 20 pM $fT_4$ and 3 mM oleic acid would, because of the increase in the extent of analogue binding, be interpreted as containing 10.6 pM $fT_4$, a bias of 47%.

The $K_{pn}[P_n]$ in the incubation conditions of this assay is estimated to be 70.

Figure 2:
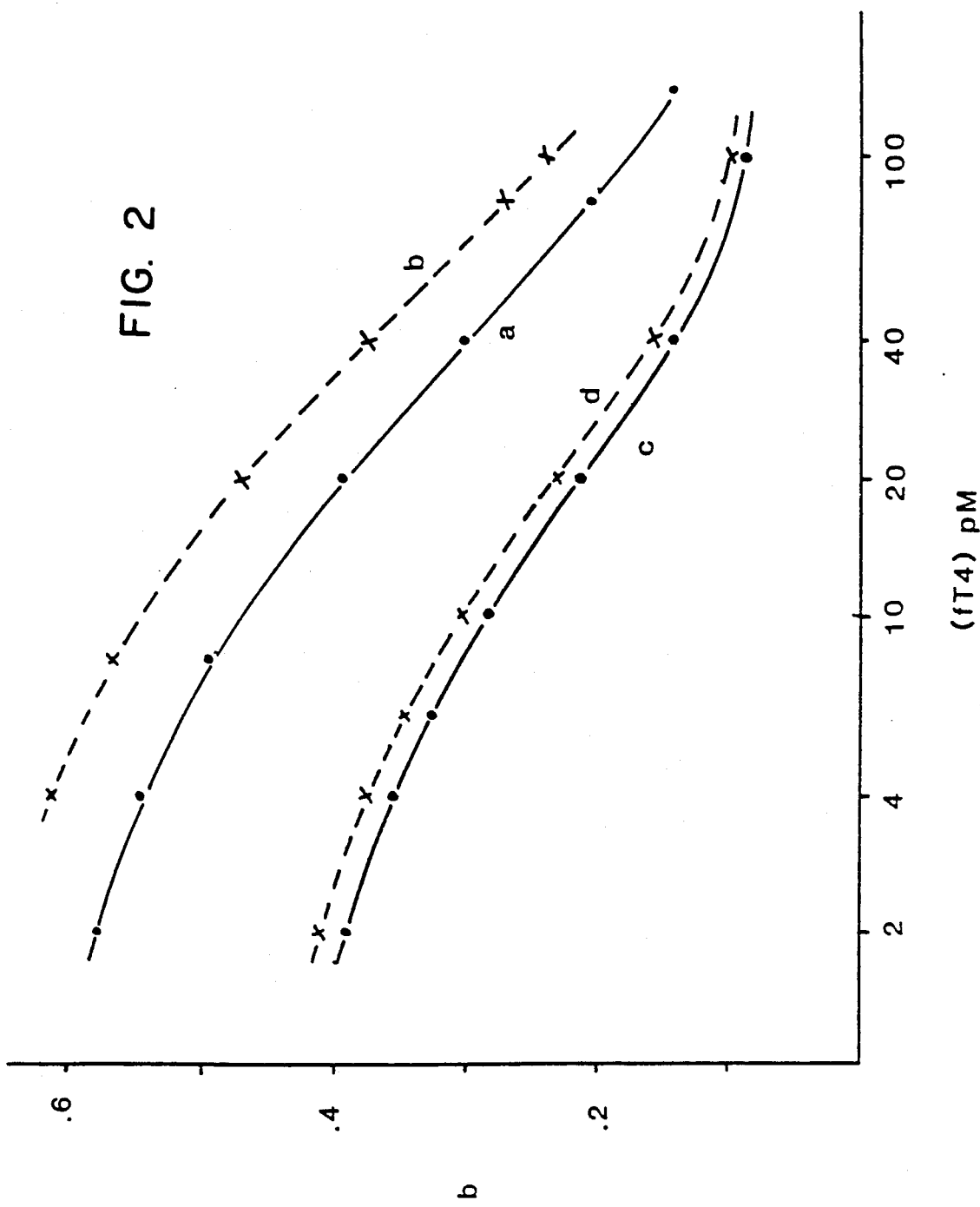
FIG. 2 is a graph showing the extent of binding of the analogue to the binding reagent.

According to the method of this invention, the additional binding agent prepared as previously described, was added to identical mixtures of antibody and antigen at a concentration of 0.2% such that $\Sigma K_x[P_x] = 150$. Again the extent of binding of the labelled analogue with the specific antibody was correlated with the $fT_4$ concentration before and after the addition of 3 mM oleic acid as shown in FIG. 2(c and d) respectively.

In this example of the invention a sample containing 20 pg/ml $fT_4$ and 1 mM oleic acid would be interpreted as containing 17 pg/ml $fT_4$, a negative bias of only 15%. Further increases in the addition of the binding agent cause additional decreases in the observed bias of the method and the required concentration of binding agent will depend on the bias permissible in the estimation of $fT_4$ for clinical reasons.

We claim:
1. A method of measuring the concentration of free ligand in a biological fluid containing the ligand both as a free ligand and as ligand reversibly bound to an endogenous binding agent, comprising
    (a) mixing a sample of the biological fluid with (1) an analogue of the ligand, (2) a specific binder with which the free ligand and the ligand analogue reversibly bind, and (3) an exogenous binding agent which reversibly binds the ligand analogue but not the ligand, either the ligand analogue or the specific binder being labelled,
    (b) incubating the resulting mixture so that the ligand and ligand analogue compete for the specific binder,
    (c) determining either (1) the amount of the labelled analogue bound to the specific binder or the exogenous binding agent; or (2) the amount of labelled specific binder bound, or not bound, to the ligand analogue, and
    (d) correlating the determined amount to the amount of free ligand present in the biological fluid.

2. A method as claimed in claim 1 wherein the contribution from the endogenous binding agents to S, wherein S is defined as one plus the sum of the products of the concentrations of each of the binding agents in the sample other than the specific binder and the respective equilibrium constants for the reactions between those binding agents and the ligand analogue, is zero or constant for all samples and the exogenous binding agent and its concentration are selected so that its contribution to S is at least 10, S being not more than 500.

3. A method as claimed in claim 1 wherein the contribution from the endogenous binding agents to S, wherein S is defined as one plus the sum of the products of the concentrations of each of the binding agents in the sample other than the specific binder and the respective equilibrium constants for the reactions between those binding agents and the ligand analogue and S varies significantly from sample to sample and the exogenous binding agent and its concentration are chosen so that its contribution to S is at least half the value of S in any sample and is comparable with or greater than the variation in S from sample to sample.

4. A method as claimed in claim 1 wherein the exogenous binding agent is a chemical reagent which binds the ligand analogue but does not substantially bind the ligand.

5. A method as claimed in claim 4 wherein the exogenous binding agent is an antibody having an affinity for the ligand analogue at least two orders of magnitude higher than its affinity for the ligand.

6. A method as claimed in claim 1 wherein the ligand analogue is labelled.

7. A method as claimed in claim 1 wherein the specific binder is labelled.

8. A method as claimed in claim 1 wherein the label is a radioactive label.

9. A method as claimed in claim 1 wherein the free ligand is a free hormone.

10. A method as claimed in claim 9 wherein the free ligand is free thyroid hormone.

11. A method as claimed in claim 1 wherein $P_1, P_2, \ldots, P_n$ are the endogenous binding agents in the biological fluid samples, $[P_1], [P_2], \ldots [P_n]$ are the concentrations of the endogenous binding agents in the biological samples, $K_P, K_{P2} \ldots K_{Pn}$ are the equilibrium constants between the free ligand analogue and the ligand analogue bound to the endogenous binding agents in the biological fluid samples, $P_X$ is the exogenous binding agent X, $[P_X]$ is the concentration of the binding agent X in the biological fluid samples, $K_{PX}$ is the equilibrium constant between the free ligand analogue and the ligand analogue bound to the binding agent X in the biological fluid samples, and $K_{PX}[P_X]$ is at least 10 and S is not more than 500, where S is $1+\Sigma K_P[P]+K_{PX}[px]$, $\Sigma K_P[P]$ is $K_{P1}[P_1]+K_{P2}[P_2]+\ldots =K_{Pn}[P_n]$, and is zero or substantially constant in all biological fluid samples to be assayed.

12. The method of claim 11 wherein S is 50–500.

13. A method as claimed in claim 1 wherein $P_1, P_2, \ldots, P_n$ are the endogenous binding agents in the biological fluid samples, $[P_1], [P_2], \ldots [P_n]$ are the concentrations of the binding agents in each of the biological fluid samples, $K_{P1}, K_{P2} \ldots K_{Pn}$ are the equilibrium constants between the free ligand analogue and the ligand analogue bound to the endogenous binding agents in the biological fluid samples, $P_x$ is the exogenous binding agent X, $[P_x]$ is the concentration of the binding agent X in the biological fluid samples, $K_{Px}$ is the equilibrium constant between the free ligand analogue and the ligand analogue bound to the binding agent X in the biological fluid samples, and $K_{Px}[P_x]$ is at least $s/2$, where S is $1+\Sigma K_P[P]+K_{PX}[px]$, $\Sigma K_P[P]$ is $K_{P1}[P_1]+K_{P2}[P_2]+ \ldots =K_{Pn}[P_n]$, and varies significantly from sample to sample of the biological fluid samples to be assayed, $K_{px}[px]$ being comparable with or greater than that variation.

* * * * *

UNITED STATES PATENT AND TRADEMARK OFFICE
CERTIFICATE OF CORRECTION

PATENT NO. : 4,745,072

DATED : May 17, 1988

INVENTOR(S) : Ekins et al.

It is certified that error appears in the above-identified patent and that said Letters Patent is hereby corrected as shown below:

In the Specification:

Column 5, line 63, "3 nM" should be --3 mM--.

Signed and Sealed this

First Day of November, 1988

Attest:

DONALD J. QUIGG

Attesting Officer

Commissioner of Patents and Trademarks